United States Patent
Liang et al.

(10) Patent No.: US 11,872,160 B2
(45) Date of Patent: Jan. 16, 2024

(54) LAMINA CRIBROSA CROSSING PRESSURE BALANCE MAINTAINER FOR CONSTANTLY BALANCING LAMINA CRIBROSA CROSSING PRESSURE DIFFERENCE, IMPLANTATION DEVICE, AND METHOD FOR BALANCING LAMINA CRIBROSA CROSSING PRESSURE DIFFERENCE

(71) Applicant: WENZHOU MEDICAL UNIVERSITY, Zhejiang (CN)

(72) Inventors: Yuanbo Liang, Zhejiang (CN); Shaodan Zhang, Zhejiang (CN); Yan Tao, Zhejiang (CN); Chengtan Liu, Zhejiang (CN)

(73) Assignee: WENZHOU MEDICAL UNIVERSITY, Zhejiang (CN)

( * ) Notice: Subject to any disclaimer, the term of this patent is extended or adjusted under 35 U.S.C. 154(b) by 615 days.

(21) Appl. No.: 17/251,671

(22) PCT Filed: Jan. 28, 2019

(86) PCT No.: PCT/CN2019/073369
§ 371 (c)(1),
(2) Date: Dec. 11, 2020

(87) PCT Pub. No.: WO2019/237749
PCT Pub. Date: Dec. 19, 2019

(65) Prior Publication Data
US 2021/0275357 A1    Sep. 9, 2021

(30) Foreign Application Priority Data

Jun. 11, 2018  (CN) .......................... 201810592156.1

(51) Int. Cl.
*A61F 9/007* (2006.01)
*A61B 90/30* (2016.01)

(52) U.S. Cl.
CPC ...... *A61F 9/00781* (2013.01); *A61F 9/00736* (2013.01); *A61B 2090/306* (2016.02)

(58) Field of Classification Search
CPC ................................... A61F 9/00781
See application file for complete search history.

(56) References Cited

U.S. PATENT DOCUMENTS

2002/0013546 A1* 1/2002 Grieshaber ......... A61F 9/00781
   604/28
2002/0143284 A1   10/2002 Tu et al.
(Continued)

FOREIGN PATENT DOCUMENTS

CN    1208602 A   2/1999
CN  102905655 A   1/2013
(Continued)

OTHER PUBLICATIONS

Tezel, G; Trinkaus, K; Wax, MB; Alterations in the morphology of lamina cribrosa pores in glaucomatous eyes, 2004, Br. J. Ophthalmol 2004; 88; 251-256 (Year: 2004).*

(Continued)

*Primary Examiner* — Catharine L Anderson
*Assistant Examiner* — Arjuna P Chatrathi
(74) *Attorney, Agent, or Firm* — Christensen, Fonder, Dardi & Herbert PLLC

(57) ABSTRACT

An implantable amina cribrosa crossing pressure balance maintainer for constantly balancing the lamina cribrosa crossing pressure difference, an implantation device, and a method for balancing the lamina cribrosa crossing pressure difference. The lamina cribrosa crossing pressure balance maintainer is placed at the lamina cribrosa to balance the (Continued)

lamina cribrosa crossing pressure difference so as to enable the deformed lamina cribrosa to recover or even reverse deformation, so that the tolerance of glaucoma patients to intraocular hypertension is improved, nerve damage caused by the lamina cribrosa crossing pressure difference is relieved and reduced, and primary factors of the glaucoma optic nerve damage are eliminated. New ideas are provided for the treatment of the glaucoma in the middle and advanced periods.

7 Claims, 2 Drawing Sheets

(56) References Cited

U.S. PATENT DOCUMENTS

| | | | |
|---|---|---|---|
| 2003/0059755 A1* | 3/2003 | D'Amico | A61F 9/007 434/272 |
| 2003/0229303 A1 | 12/2003 | Haffner et al. | |
| 2004/0254517 A1* | 12/2004 | Quiroz-Mercado | A61F 9/00781 604/8 |
| 2008/0228127 A1* | 9/2008 | Burns | A61F 9/00781 604/9 |
| 2009/0210053 A1* | 8/2009 | Schachar | A61N 1/36046 623/4.1 |
| 2009/0227933 A1* | 9/2009 | Karageozian | A61F 9/0008 604/521 |
| 2010/0274259 A1* | 10/2010 | Yaron | A61M 27/002 604/8 |
| 2012/0165720 A1* | 6/2012 | Horvath | A61F 9/00781 604/8 |
| 2014/0052140 A1* | 2/2014 | Sayegh | A61B 17/0231 606/107 |

FOREIGN PATENT DOCUMENTS

| | | | | |
|---|---|---|---|---|
| CN | 105748193 A | 7/2016 | | |
| CN | 106963543 A | 7/2017 | | |
| CN | 108743014 A | 11/2018 | | |
| WO | WO-2011089605 A2 * | 7/2011 | | A61F 9/00781 |

OTHER PUBLICATIONS

Park HYL; Jeon SH; Park CK; Enhanced Depth Imaging Detects Lamina Cribrosa Thickness Differences in Normal Tension Glaucoma and Primary Open-Angle Glaucoma, 2012; Ophthalmology 2012; 119;10-20 (Year: 2012).*

Spandau U; Pavlidis M; 27-Gauge Vitrectomy Minimal Sclerotomies for Maximal Results, Chapter 3—Usage of 27G Instruments, 2015, Springer International Publishing; 43-57 (Year: 2015).*

* cited by examiner

LAMINA CRIBROSA CROSSING PRESSURE BALANCE MAINTAINER FOR CONSTANTLY BALANCING LAMINA CRIBROSA CROSSING PRESSURE DIFFERENCE, IMPLANTATION DEVICE, AND METHOD FOR BALANCING LAMINA CRIBROSA CROSSING PRESSURE DIFFERENCE

RELATED APPLICATIONS

The present application is a National Phase entry of PCT Application No. PCT/CN2019/073369, filed Jan. 28, 2019, which claims priority to Chinese Patent Application No. 201810592156.1, filed Jun. 11, 2018, the disclosures of which are hereby incorporated by reference herein in their entirety.

FIELD OF THE INVENTION

The invention mainly relates to the technical field of glaucoma treatment, in particular to a trans-lamina cribrosa pressure balance maintainer for continuously balancing trans-lamina cribrosa pressure difference of glaucoma patients, an implantation device and a method for balancing trans-lamina cribrosa pressure difference.

BACKGROUND OF THE INVENTION

As the largest irreversible blindness eye disease in the world, glaucoma is mainly caused by pathological high intraocular pressure and it is a progressive optic neuropathy characterized by apoptosis of retinal ganglion cells and gradual loss of visual function. Glaucoma is an age-related eye disease. With the increase in life expectancy, the prevalence of glaucoma will increase. By 2020, the number of glaucoma patients will have increased to 80 million and the number of glaucoma patients in China will reach 25 million, moreover, the age of onset tends to be younger. Glaucoma has a high incidence of blindness, and the increase of pathological intraocular pressure is recognized as the main reason for the occurrence and development of glaucoma, but clinically, the intraocular pressure of patients with ocular hypertension exceeds the upper limit of statistical normal value, and the damage of optic nerve and visual field is normal after long-term follow-up. However, in patients with normal pressure glaucoma (NPG), their intraocular pressure is in a normal range, but typical glaucoma optic nerve atrophy and visual field defect occur. Animal experiments have also found that the gradual reduction of intracranial pressure through lumbar cistern cerebrospinal fluid shunt can lead to changes in the fundus oculi of rhesus monkeys similar to glaucoma. In addition, astronauts living in microgravity for a long time showed high intracranial pressure (ICP) and visual dysfunction and have ganglion cell death and corresponding manifestations. Therefore, the above phenomenon cannot be explained from the perspective of intraocular pressure (ICP) alone. Recent studies have shown that increased trans-lamina cribrosa pressure difference may be one of the causes of normal pressure glaucoma. Many scholars have found that the cerebrospinal fluid pressure in patients with primary open-angle glaucoma and normal pressure glaucoma is low, while the cerebrospinal fluid pressure in patients with ocular hypertension is high. It is suggested that the increase of trans-lamina cribrosa pressure difference may be an important etiological mechanism of glaucoma optic nerve damage.

Under normal circumstances, the orbit of the human eye and the cranial cavity are separated by a thin bone lamella, while in the posterior pole of the orbit, there is an optic canal structure for the optic nerve fiber bundle to penetrate from the eye to the cerebral cortex. A point where the optic nerve meets is the optic papilla, while the lamina cribrosa is a funnel-shaped physiological structure in the center of the optic papilla, which is composed of more than 10 layers of thin plate comprised of regularly arranged glial tissue with holes. Therefore, the orbit and cranial cavity are separated by only several layers of glial tissue near the optic papilla. In healthy people, the intraocular pressure is in the range of 10-21 mm Hg, while the intracranial pressure is 5-15 mm Hg, both of which maintain the stability of the lamina cribrosa near the optic papilla.

The lamina cribrosa is the primary site of optic nerve damage in glaucoma patients. By the experimental increase of intraocular pressure in monkeys, it was found that the transport at axon of the lamina cribrosa of the optic papilla was blocked and the organelles in the nerve cells were swollen. In addition, it was found that the astrocytes in the lamina cribrosa were activated, which were mainly manifested as the hypertrophy of astrocytes in the anterior area of the lamina cribrosa, the thickening and elongation of the neurite, the cell bodies of astrocytes in the lamina cribrosa became round and the neurites were absent. Astrocytes also showed that there were fewer glial columns in the front optic papilla area and migrated to the nerve bundles in the lamina cribrosa, which weakened the supporting function of astrocytes to nerve axons. The reduction of connective tissue density on the upper and lower sides of lamina cribrosa corresponds well to the marked hourglass-shaped atrophy of the optic nerve. Furthermore, the extracellular matrix of lamina cribrosa in patients with advanced glaucoma is extensively reconstituted. The main manifestation was the increase of extracellular matrix in the lamina cribrosa, mainly the increase of the expression of type IV collagen and connexin, while the decrease and rupture of elastic fibers. The anterior area of lamina cribrosa was convex, the nerve bundle disappeared, type IV collagen fiber filled most of the space, the lamina cribrosa collapsed, overlapped and fused. This alteration of the lamina cribrosa reduces its compliance and resiliency, causing reconstruction of the optic papilla tissue and alteration of the microenvironment, resulting in progressive and irreversible loss of axons of retinal ganglion cells. Increased trans-lamina cribrosa pressure difference increases the pressure gradient experienced by the lamina cribrosa, thereby increasing the mechanical forces (such as shear forces) experienced by the optic nerve fibers, the blood supply of RGCs is also blocked, while the forward and reverse axoplasm flow of RGCs is blocked. In addition, the biomechanics of lamina cribrosa was studied by establishing digital 3D geometric models (idealized human eyeball), each of which consists of 900 finite elements, in order to evaluate the effects of different levels of IOP on optic papilla with different sizes and shapes and on scleral thickness around optic papilla. The results showed that different levels of intraocular pressure produced maximum pressure at the lamina cribrosa, and gradually decreased along lamina cribrosa, sclera around optic papilla and posterior scleral region. For example, the same intraocular pressure in the channel the scleral optic nerve passing through is 30-100 times the intraocular pressure, while in the ethmoid bundle of the lamina cribrosa, it can reach 50-180 times the intraocular pressure. This proves that the optic papilla is exposed to a "high pressure environment". Therefore, in patients with glaucoma, the trans-lamina cribrosa pressure difference increases, which makes the eyeball wall tension pull the lamina cribrosa longitudinally, which is prone to structural deformation and compression and the outward movement of the posterior part of the lamina cribrosa, as well as the thinning and reduction of connective tissue and changes in the shape and size of the lamina cribrosa pore. These changes directly lead to the extrusion of the optic nerve fiber bundle in the lamina cribrosa pore or destroy the normal transport of the axoplasm flow, and the neurotrophic factors cannot be transported to the ganglion cells, resulting in the death of the ganglion cells and finally the corresponding visual field defect. In addition, the increase of lamina cribrosa pressure also squeezes the adjacent blood vessels and blocks the blood flow, which further increases the optic nerve damage of glaucoma due to the loss of nerve and glial cell nutrition and the accumulation of metabolites.

In addition, anti-glaucoma surgery is widely used in clinic: trabeculectomy, simple cataract surgery, combined surgery of glaucoma and cataract, transscleral cylophotocoagulation. Trabeculectomy is a routine classical operation for glaucoma, and its complications are still inevitable, such as low intraocular pressure, shallow anterior chamber, choroidal detachment and cystoid macular edema in the early stage. Surgery failure may occur in the late stage, and the problem of filtering bleb scarring can reach 50% over 5 years. The complications caused by filtering bleb include filtering bleb leakage, infection, prolapse and the effect of filtering bleb on the structure and function of ocular surface. In the past five years, the improvement of surgical methods has been further deepened. More and more attention has been paid to the operation characterized by intraocular filtration and minimally invasive drainage. For example, Trabectome and I-Stent surgery are the representatives of internal Schlemm's surgery; Canaloplasty and dilatation iTRACK are the representatives of ab-externo canaloplasty, and Canaloplasty has the advantages of being minimally invasive, less injurious, and providing good stability of the anterior chamber, and promoting safety and rapid recovery. Non-filtering bleb dependence can reconstruct the natural outflow channel of aqueous humor without forming filtering blebs and avoiding filtering bleb-related complications, but it is only suitable for primary open-angle glaucoma. Therefore, it is particularly important to find new surgical methods for the treatment of glaucoma. The surgical method to continuously balance the trans-lamina cribrosa pressure difference in glaucoma patients is applicable to all primary and secondary glaucoma, including normal pressure glaucoma and ocular hypertension, as well as various diseases due to imbalanced pressure differential across the lamina cribrosa. The implantation of the trans-lamina cribrosa pressure balance maintainer which continuously balances the trans-lamina cribrosa pressure difference can reduce the trans-lamina cribrosa pressure difference, restore or even reverse the deformation of the lamina cribrosa. In addition, this surgical method can also improve the tolerance of glaucoma patients to high intraocular pressure, delay and reduce the nerve damage caused by the pressure difference across the lamina cribrosa, and remove the primary factors of glaucoma optic nerve damage.

SUMMARY OF THE INVENTION

In order to solve the defects and deficiencies of the prior art, the invention provides an implantable trans-lamina cribrosa pressure balance maintainer for continuously balancing the trans-lamina cribrosa pressure difference and an implant device and a method for balancing the trans-lamina cribrosa pressure difference, so as to balance the trans-lamina cribrosa pressure difference, restore or even reverse the lamina cribrosa deformation, improve the tolerance of glaucoma patients to high intraocular pressure, delay and reduce the nerve damage caused by the pressure difference across the lamina cribrosa, and remove the primary factors of glaucoma optic nerve damage.

The technical solution adopted by the invention is as follows: a trans-lamina cribrosa pressure balance maintainer for continuously balancing trans-lamina cribrosa pressure difference. The pressure balance maintainer comprises a balance maintainer body, wherein a limiting plate is provided at the bottom of the balance maintainer body, a maintaining channel is provided on the limiting plate, the front end of the maintaining channel is the top, a first drainage hole is provided on the top, a through flow channel is provided in the middle of the maintaining channel, and the first drainage hole is in communication with the flow channel, the flow channel penetrates through the maintaining channel and the limiting plate at the bottom, the bottom of the limiting plate is provided with a guide groove, and the guide groove is in communication with the flow channel.

A plurality of second drainage holes are provided on the side wall of the maintaining channel, and the second drainage holes are non-collinearly arranged.

The side wall of the maintaining channel is provided with five second drainage holes, and the two of the five second drainage holes are non-collinear arranged.

The first drainage hole has a pore size of 200 μm, and the second drainage holes have a pore size of 10 μm.

The position of the second drainage hole provided on the side wall of the maintaining channel is at least 1200 μm away from the limiting plate.

The length of the maintaining channel is 1800-2000 μm.

The limiting plate is provided in a disc shape, the diameter of the limiting plate is larger than that of the maintaining channel, and the diameter of the limiting plate is 300 μm.

The invention also relates to an implanting device for a trans-lamina cribrosa pressure balance maintaining device for continuously balancing trans-lamina cribrosa pressure difference, comprising an injecting mechanism with a puncturing structure that is provided at the front end of the injecting mechanism; the trans-lamina cribrosa pressure balance maintainer is insertable in the puncturing device and is used for performing injection puncturing utilizing the injection mechanism and the puncturing structure and to puncture the lamina cribrosa in the fundus oculi.

A method for continuously balancing trans-lamina cribrosa pressure difference by utilizing a trans-lamina cribrosa pressure balance maintainer comprises the following steps of forming and maintaining a new balance of the front pressure and the rear pressure across the lamina cribrosa by puncturing the eye bottom lamina cribrosa and placing the trans-lamina cribrosa pressure balance maintainer in the pore of, or through, the lamina cribrosa to balance the trans-lamina cribrosa pressure difference.

A method for continuously balancing the trans-lamina cribrosa pressure difference comprises the following steps that a trocar is inserted at an 8 o'clock position away from the corneal limbal 3.5 mm with taking a measuring scale; after the trocar handle is removed, the sealing cap is placed to ensure the sealing integrity of the eyeball, and then trocars are inserted at 2 o'clock and 10 o'clock position respectively, and the sealing caps are also placed; the trocar at 8 o'clock position is removed, and the intraocular infusing device is connected to maintain the balance of intraocular pressure during the operation; the sealing caps of the trocars at 2 o'clock and 10 o'clock position were removed; the vitrectomy head and the optical fiber were put into the eye for vitrectomy, and the instrument for vitrectomy was extracted; the trans-lamina cribrosa pressure balance maintainer entered the vitreous cavity of the excised vitreous body from the 2 o'clock position, then located at the optic papilla, so as to puncture the lamina cribrosa while avoiding blood vessels; after successful implantation of the pressure balance maintainer, the puncture instrument was withdrawn, leaving the pressure balance maintainer in the lamina cribrosa and normal saline was used to fill the eyeball to ensure normal intraocular pressure and complete the operation.

The invention has the beneficial effects that the invention provides a trans-lamina cribrosa pressure balance maintainer for continuously balancing the trans-lamina cribrosa pressure difference and an implanting device and a method for balancing the trans-lamina cribrosa pressure difference, placing the trans-lamina cribrosa pressure balance maintainer at the lamina cribrosa, so as to balance the trans-lamina cribrosa pressure difference, restore or even reverse the lamina cribrosa deformation, improve the tolerance of glaucoma patients to high intraocular pressure, delay and reduce the nerve damage caused by the pressure difference across the lamina cribrosa. It provides new ideas for the treatment of advanced glaucoma.

In the FIGS., 1-a balance maintainer body, 2-a limiting plate, 3-a maintaining shaft, 21-a flow guide groove, 31-a top, 32-a first drainage hole, 33-a flow channel and 34-second drainage holes.

DETAILED DESCRIPTION OF THE INVENTION

In order to better understand the technical content of the present invention, the following embodiments are specifically described in detail.

Figure 1:
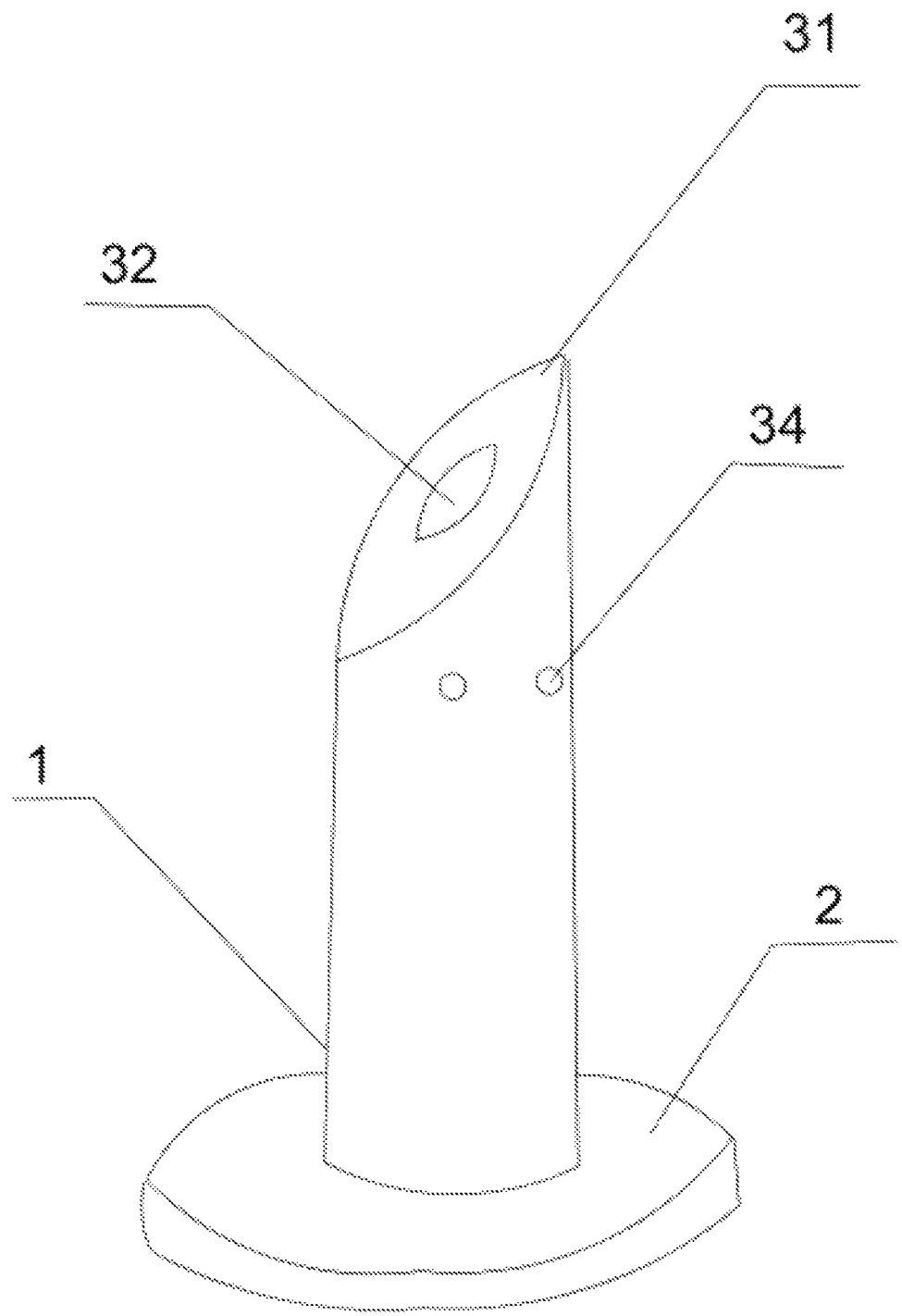
FIG. 1 is a schematic view of the structure of a trans-lamina cribrosa pressure balance maintainer according to the present invention.
Figure 2:
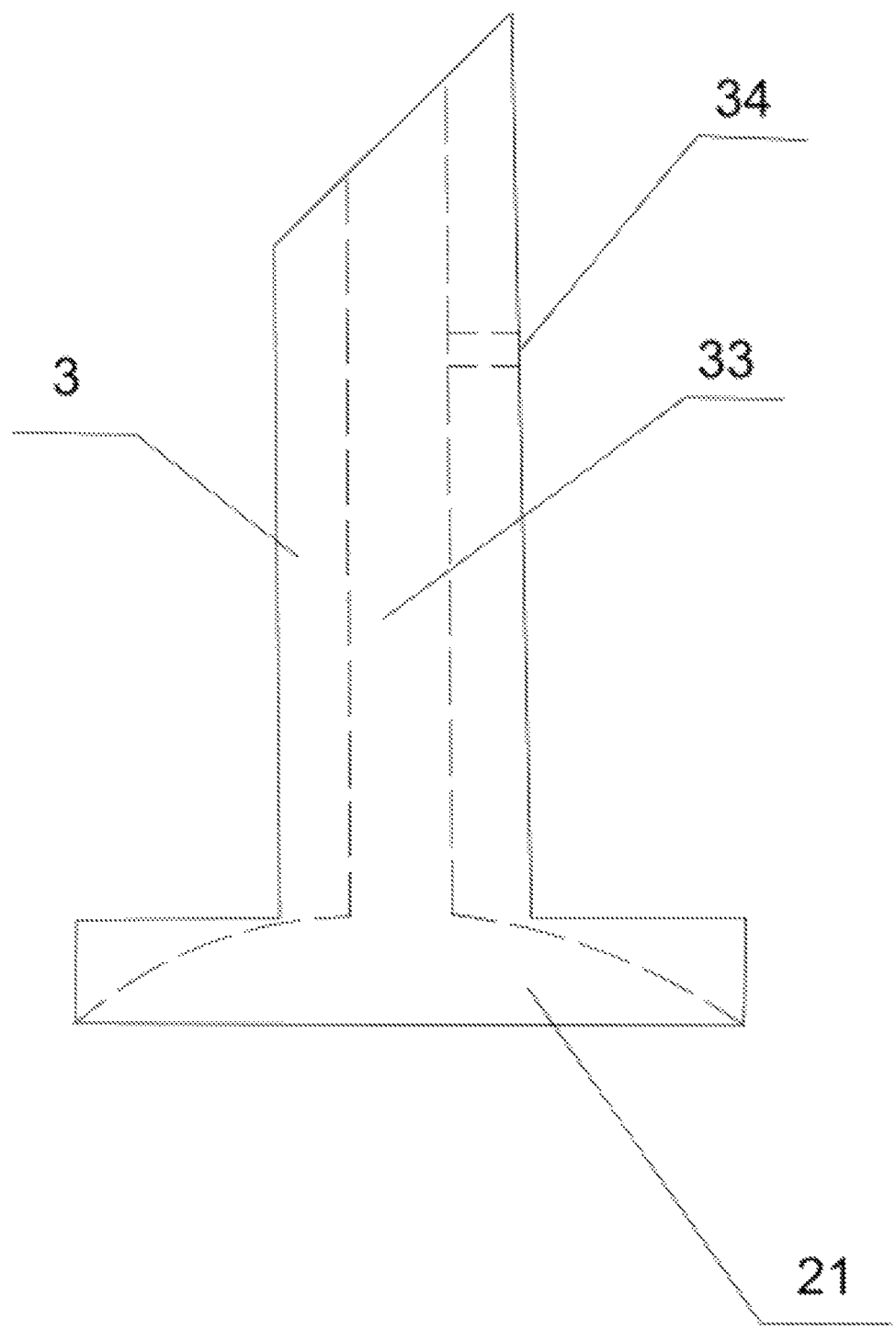
FIG. 2 is a cross-sectional view of the structure of a trans-lamina cribrosa pressure balance maintainer according to the present invention.

As shown in FIGS. 1 and 2, a trans-lamina cribrosa pressure balance maintainer 1 for continuously balancing trans-lamina cribrosa pressure difference is depicted. The balance maintainer 1, is provided with a limiting plate 2, the limiting plate 2 is in a disc-shaped arrangement or other shape structure design, the diameter of the limiting plate 2 is larger than the diameter of a maintaining shaft 3, and in an embodiment, the diameter of the limiting plate 2 is about 300 μm; for limiting the trans-lamina cribrosa pressure balance maintainer 1 in the hole of the lamina cribrosa, the limiting plate 2 is provided with a maintaining shaft 3, the maintaining shaft 3 can be designed in various shapes with channel structures, the front end of the maintaining shaft 3 includes a top 31, the top 31 is provided with a first drainage hole 32, and in an embodiment, the pore size of the first drainage hole 32 is about 200 μm; a through flow channel 33 is provided in the middle of the maintaining shaft 3, and the first drainage hole 32 is in communication with the flow channel 33; the flow channel 33 penetrates through the maintaining shaft 3 and the limiting plate 2 at the bottom, the bottom of the limiting plate 2 is provided with a guide groove 21, and the guide groove 21 is in communication with the flow channel 33. A plurality of second drainage holes 34 are provided on the side wall of the maintaining shaft 3, and the second drainage holes 34 are non-collinearly arranged. In an embodiment, the second drainage holes 34 have a pore size of about 10 μm.

The side wall of the maintaining shaft 3 is provided with about five second drainage holes 34, and the two of the five second drainage holes 34 are non-collinearly arranged. The non-collinear arrangement between the second drainage holes 34 prevents tissue growth into the flow channels of the trans-lamina cribrosa pressure balance maintainer. The second drainage holes 34 may be disposed at any angle other than 180° between them.

The position of the second drainage holes 34 provided on the side wall of the maintaining shaft 3 is at least 1200 μm away from the limiting plate 2. The normal human lamina cribrosa is approximately 350 μm thick and the second drainage holes 34 are positioned at least 1200 μm from the limiting plate 2 for drainage.

The length of the maintaining shaft 3 may be set to at least 1200 μm, with an optimal length of 1800-2000 μm.

The trans-lamina cribrosa pressure balance maintainer 1 is made of a titanium alloy material or any other material with good biocompatibility and the drainage function.

The invention also relates to an implanting device for a trans-lamina cribrosa pressure balance maintaining device 1 for continuously balancing trans-lamina cribrosa pressure difference. The implanting device comprises an injecting mechanism, a puncturing structure is provided at the front end of the injecting mechanism; the trans-lamina cribrosa pressure balance maintainer 100 is further inserted into the puncturing device and is used for performing an injection puncture using the injection mechanism and the puncturing structure and is seated in the lamina cribrosa in the fundus oculi. The puncturing device punctures the lamina cribrosa through the puncturing structure by pressing an elastic device of the injecting mechanism, and penetrates the trans-lamina cribrosa pressure balance maintainer 1 through the eye bottom lamina cribrosa, so that the front pressure and the rear pressure of the lamina cribrosa are balanced.

The invention also relates to a method for continuously balancing trans-lamina cribrosa pressure difference by utilizing a trans-lamina cribrosa pressure balance maintainer 1 that comprises the following steps of forming and maintaining a new balance of intraocular pressure and intracranial pressure by puncturing the eye bottom lamina cribrosa and placing the trans-lamina cribrosa pressure balance maintainer 1 in a pore of the lamina cribrosa to balance the trans-lamina cribrosa pressure difference.

A method for continuously balancing the trans-lamina cribrosa pressure difference comprises the following steps: a trocar is inserted at an 8 o'clock position away from the corneal limbal 3.5 mm with taking a measuring scale; after the handle is removed, the sealing cap is placed to ensure the sealing integrity of the eyeball, and then trocars are inserted at 2 o'clock and o'clock position respectively, and the sealing cap is also placed; the trocar at the 8 o'clock position is removed, and intraocular infusing is performed to maintain the balance of intraocular pressure during the operation; the sealing caps of the trocar at 2 o'clock and 10 o'clock position are removed, the vitrectomy head and the optical fiber are put into the two trocars so as to perform a vitrectomy; the instrument for vitrectomy is extracted; the trans-lamina cribrosa pressure balance maintainer enters the vitreous cavity of the excised vitreous body from 2 o'clock position, located in the optic papilla, and punctures the lamina cribrosa avoiding blood vessels; after successful implantation of the pressure balance maintainer, withdrawing the puncture instrument and using normal saline to fill the eyeball to ensure normal intraocular pressure and completing the operation.

Increased trans-lamina cribrosa pressure difference may lead to glaucoma, which is a mechanical hypothesis of optic nerve injury in patients with glaucoma. Balancing the trans-lamina cribrosa pressure difference can remove the primary factors of optic nerve damage in glaucoma. Therefore, the invention provides a permanent implanted puncturing device for continuously balancing the trans-lamina cribrosa pressure difference, a puncturing implantation device and a method for balancing the trans-lamina cribrosa pressure difference.

The above-mentioned embodiments are merely preferred embodiments of the present invention, and the scope of the present invention is not limited to the above-mentioned embodiments, and all technical solutions falling within the spirit of the present invention fall within the scope of the present invention. It should be noted that those skilled in the art will appreciate that various modifications and adaptations can be made without departing from the spirit and scope of the present invention, such modifications and alterations are intended to be regarded as the scope of this invention.

The invention claimed is:

1. A method for continuously balancing trans-lamina cribrosa pressure difference by utilizing a trans-lamina cribrosa pressure balance maintainer, comprising the following steps of forming and maintaining a new balance of the front and the rear of the lamina cribrosa by puncturing the lamina cribrosa of the eye of a patient and placing the trans-lamina cribrosa pressure balance maintainer in a pore of the lamina cribrosa to balance the trans-lamina cribrosa pressure difference, wherein the trans-lamina cribrosa pressure balance maintainer comprises a limiting plate that is provided at a bottom portion of the trans-lamina cribrosa pressure balance maintainer, a maintaining shaft that is connected to the limiting plate, a front end of the maintaining channel forming a top portion of the trans-lamina cribrosa pressure balance maintainer, a first drainage hole is defined at the top portion, a through flow channel is defined in a middle of the maintaining shaft, and the first drainage hole is in communication with the flow channel, the flow channel penetrates through the maintaining shaft and the limiting plate at the bottom portion of the trans-lamina cribrosa pressure balance maintainer, a bottom of the limiting plate is provided with a guide groove, and the guide groove is in communication with the flow channel, the maintaining shaft includes a side wall that defines a plurality of second drainage holes, and the plurality of second drainage holes are non-collinearly arranged, the first drainage hole has a pore size of 200 μm and the second drainage hole has a pore size of 10 μm.

2. The method for continuously balancing the trans-lamina cribrosa pressure difference by utilizing a trans-lamina cribrosa pressure balance maintainer of claim 1, further comprising the following steps of:
inserting a trocar into the eye at an 8 o'clock position, and 3.5 mm away from a corneal limbal of the eye;
removing a handle of the trocar and placing a sealing cap on the trocar to ensure the sealing integrity of the eye;
inserting trocars at a 2 o'clock and a 10 o'clock position, respectively;
placing sealing caps on the trocars at the trocars at the 2 o'clock and a 10 o'clock positions;
removing the trocar at the 8 o'clock position, and
performing intraocular infusing to maintain a balance of intraocular pressure;
removing the sealing caps of the trocars at the 2 o'clock and 10 o'clock positions;
inserting a vitrectomy instrument and an optical fiber for performing a vitrectomy;
extracting the vitrectomy instrument after vitrectomy;
causing the trans-lamina cribrosa pressure balance maintainer to enter the vitreous cavity of the excised vitreous body from the 2 o'clock position and to be located in the optic papilla;
puncturing the lamina cribrosa while avoiding blood vessels;
after placement of the trans-lamina cribrosa pressure balance maintainer, withdrawing the puncture instrument; and
using normal saline to fill the eye to ensure normal intraocular pressure.

3. The method for continuously balancing trans-lamina cribrosa pressure difference by a trans-lamina cribrosa pressure balance maintainer of claim 1, wherein the side wall of the maintaining shaft is provided with five second drainage holes, and two of the five second drainage holes are non-collinearly arranged.

4. The method for continuously balancing trans-lamina cribrosa pressure difference by a trans-lamina cribrosa pressure balance maintainer of claim 1, wherein a position of the second drainage holes in the side wall of the maintaining channel are each at least 1200 μm away from the limiting plate.

5. The method for continuously balancing trans-lamina cribrosa pressure difference by a trans-lamina pressure balance maintainer of claim 1, wherein a length of the maintaining shaft is 1800-2000 μm.

6. The method for continuously balancing trans-lamina cribrosa pressure difference by a trans-lamina pressure balance maintainer of claim 1, wherein the limiting plate forms a disc shape, a diameter of the limiting plate is larger than a diameter of the maintaining shaft, and the diameter of the limiting plate is 300 μm.

7. An implanting device of a trans-lamina cribrosa pressure balance maintaining device for continuously balancing trans-lamina cribrosa pressure difference, comprising an injecting mechanism, a puncturing structure a front end of the injecting mechanism, and wherein the trans-lamina cribrosa pressure balance maintainer of claim 1 is further provided in the puncturing device and is used for performing pushing, injection and puncture through the injecting mechanism and the puncturing structure, so as to be implanted in the lamina cribrosa in a fundus oculi.

* * * * *